United States Patent
KM et al.

(10) Patent No.: US 9,983,580 B2
(45) Date of Patent: May 29, 2018

(54) AUTOMATIC DATABASE FILTERING SYSTEM UTILIZING ROBOTIC FILTERS

(71) Applicant: International Business Machines Corporation, Armonk, NY (US)

(72) Inventors: Shankar KM, Bangalore (IN); Aiswarya L. Mohanasundaram, Bangalore (IN)

(73) Assignee: International Business Machines Corporation, Armonk, NY (US)

(*) Notice: Subject to any disclaimer, the term of this patent is extended or adjusted under 35 U.S.C. 154(b) by 0 days. days.

(21) Appl. No.: 15/588,827

(22) Filed: May 8, 2017

(65) Prior Publication Data

US 2017/0261979 A1    Sep. 14, 2017

Related U.S. Application Data

(63) Continuation of application No. 15/064,769, filed on Mar. 9, 2016.

(51) Int. Cl.
| | |
|---|---|
| *G05D 3/00* | (2006.01) |
| *G05D 1/00* | (2006.01) |
| *B25J 9/16* | (2006.01) |
| *F24F 13/28* | (2006.01) |
| *H05K 7/14* | (2006.01) |
| *G01N 33/00* | (2006.01) |

(Continued)

(52) U.S. Cl.
CPC ......... *G05D 1/0038* (2013.01); *B01D 46/442* (2013.01); *B01D 46/46* (2013.01); *B25J 9/1664* (2013.01); *B25J 9/1697* (2013.01); *F24F 13/28* (2013.01); *G01N 33/0034* (2013.01); *G01N 33/0075* (2013.01); *H05K 7/1497* (2013.01); *B01D 2273/16* (2013.01); *B01D 2279/51* (2013.01)

(58) Field of Classification Search
CPC ..... G05D 1/0038; B01D 46/442; B01D 46/46
See application file for complete search history.

(56) References Cited

U.S. PATENT DOCUMENTS

| | | |
|---|---|---|
| 7,031,802 B2 | 4/2006 | Bash et al. |
| 8,751,043 B2 | 6/2014 | Guo et al. |
| 2012/0111190 A1 | 5/2012 | Dariavach et al. |

(Continued)

FOREIGN PATENT DOCUMENTS

| | | |
|---|---|---|
| CN | 103322623 A | 9/2013 |
| WO | 2014113713 A1 | 7/2014 |

OTHER PUBLICATIONS

Mell et al., "The NIST Definition of Cloud Computing," National Institute of Standards and Technology, Sep. 2011, p. 1-3, Special Publication 800-145.

(Continued)

*Primary Examiner* — Adam M Alharbi
(74) *Attorney, Agent, or Firm* — Christopher M. Coy

(57) ABSTRACT

A plurality of air data may be collected by a sensor within a data center. The plurality of air data is received by a processor. At least a portion of the received plurality of air data corresponding to at least one zone within the data center may be determined to satisfy a threshold. Coordinates of a geographical location associated with the zone that includes the sensor may be transmitted to a robotic filter. The robotic filter can be dispatched to the transmitted geographic location to filter the zone.

7 Claims, 10 Drawing Sheets

(51) Int. Cl.
*B01D 46/44* (2006.01)
*B01D 46/46* (2006.01)

(56) References Cited

U.S. PATENT DOCUMENTS

| | | | |
|---|---|---|---|
| 2013/0231779 A1 | 9/2013 | Purkayastha et al. | |
| 2014/0105589 A1* | 4/2014 | Samuels | F16F 7/00 396/421 |
| 2016/0148963 A1* | 5/2016 | Creazzo | H01L 27/14627 257/432 |
| 2017/0160201 A1* | 6/2017 | Nishizawa | G01N 21/65 |

OTHER PUBLICATIONS

Shankar KM, et al., "Automatic Database Filtering System Utilizing Robotic Filters," U.S. Appl. No. 15/064,769, filed Mar. 9, 2016.
List of IBM Patents or Patent Applications Treated as Related, May 5, 2017, 2 pgs.

* cited by examiner

AUTOMATIC DATABASE FILTERING SYSTEM UTILIZING ROBOTIC FILTERS

BACKGROUND

The present disclosure relates to the field of data processing, and more specifically, to robot control.

A data center is a facility used to house computer systems and associated components, such as computer servers and database systems. Data centers generally include computer hardware racks, backup power supplies, and data communications connections. Data centers can house sensitive information, and, therefore, data centers can further include environmental controls (e.g., air conditioning and fire suppression) and various security devices. Large data centers can be industrial scale operations using as much electricity as a small town.

SUMMARY

According to one embodiment, a processor-implemented method for filtering a plurality of air is provided. The processor-implemented method may include receiving, by a processor, a plurality of air data collected by a sensor within a data center. The processor-implemented method may further include determining that at least a portion of the plurality of received air data corresponding to at least one zone within the data center satisfies a threshold. The processor-implemented method may further include transmitting coordinates of a geographical location associated with the zone that includes the sensor to a robotic filter. The processor-implemented method may further include dispatching the robotic filter to the transmitted geographic location to filter the zone.

According to another embodiment, a computer system for filtering a plurality of air is provided. The computer system may include one or more processors, one or more computer-readable memories, one or more computer-readable tangible storage devices, and program instructions stored on at least one of the one or more storage devices for execution by at least one of the one or more processors via at least one of the one or more memories, whereby the computer system is capable of performing a processor-implemented method. The processor-implemented method may include receiving, by a processor, a plurality of air data collected by a sensor within a data center. The processor-implemented method may further include determining that at least a portion of the plurality of received air data corresponding to at least one zone within the data center satisfies a threshold. The processor-implemented method may further include transmitting coordinates of a geographical location associated with the zone that includes the sensor to a robotic filter. The processor-implemented method may further include dispatching the robotic filter to the transmitted geographic location to filter the zone.

According to yet another embodiment, a computer program product for filtering a plurality of air is provided. The computer program product may include one or more computer-readable storage devices and program instructions stored on at least one of the one or more tangible storage devices, the program instructions executable by a processor. The computer program product may include program instructions to receive, a plurality of air data collected by a sensor within a data center. The computer program product may further include program instructions to determine that at least a portion of the plurality of received air data corresponding to at least one zone within the data center satisfies a threshold. The computer program product may further include program instructions to transmit coordinates of a geographical location associated with the zone that includes the sensor to a robotic filter. The computer program product may further include program instructions to dispatch the robotic filter to the transmitted geographic location to filter the zone.

BRIEF DESCRIPTION OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
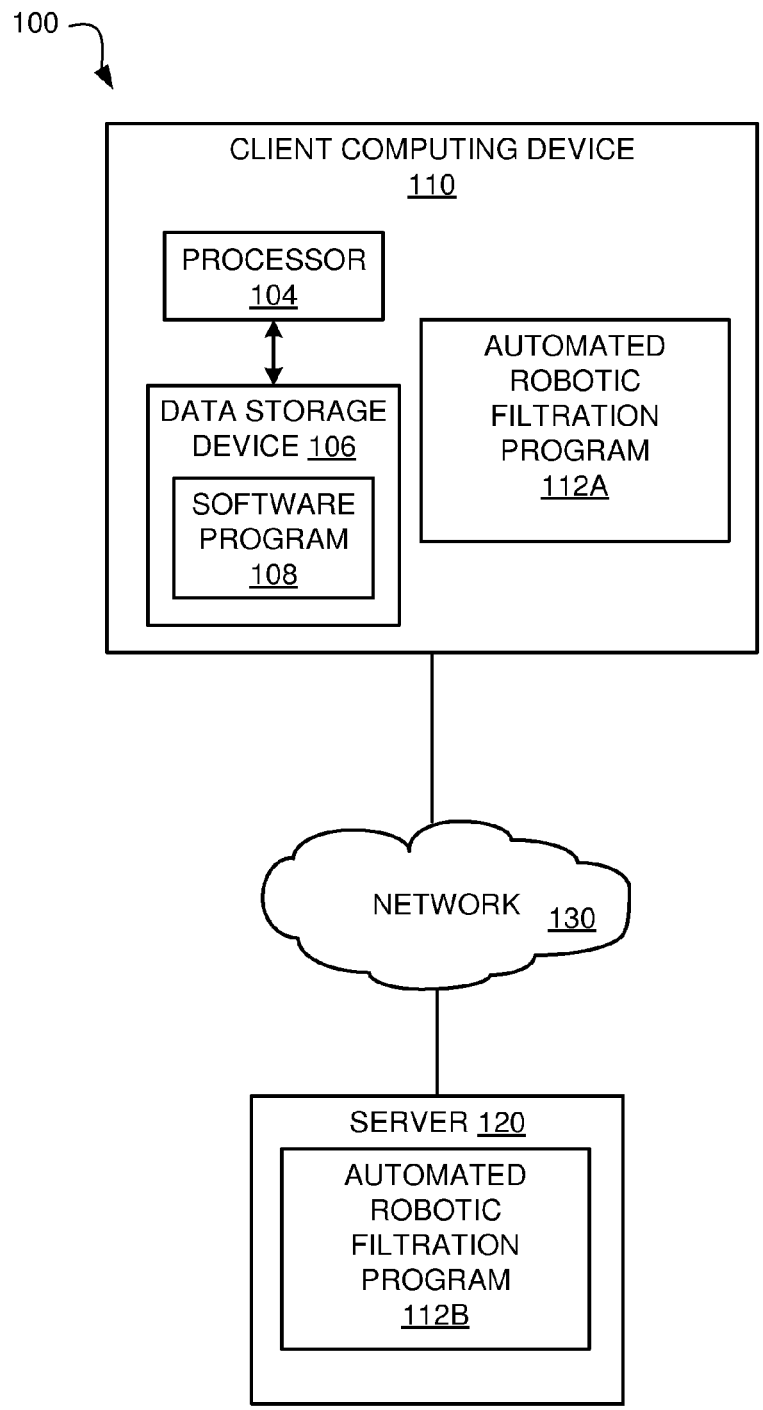
FIG. 1 is an exemplary networked computer environment, in accordance with one embodiment of the present invention.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

Embodiments of the present disclosure relate to the field of data processing, and more specifically, to robot control. While the present disclosure is not necessarily limited to such applications, various aspects of the disclosure may be appreciated through a discussion of various examples using this context. The following described exemplary embodiments provide a system, method, and computer program product to, among other things, automatically filter a data center based on receiving collected air data that satisfies a threshold. Therefore, the present embodiment has the capacity to improve the technical field of robot control by automatically instructing robots to filter air within a data center where the air may be contaminated. More specifically, the present embodiment may allow for more efficient energy expenditure in data centers by relocating mobile filters to a contaminated zone of the data center. Furthermore, the present embodiment may be capable of reacting to changing contamination sources within a data center.

Current technologies and applications that are capable of mapping and exploring data centers include IBM® Mobile Management Technology (MMT) (IBM MMT and all IBM MMT-based trademarks and logos are trademarks or registered trademarks of International Business Machines Corporation and/or its affiliates). MMT is an automated system that can evaluate the environment (e.g., temperature) of data centers. Furthermore, MMT can depict temperature distributions within the data center in a digital representation based on the environmental evaluation. This representation can be transmitted to and displayed within a user interface (UI).

Computers in data centers often experience high failure rates due to damage of computer hardware components by airborne pollutants (e.g., chemical gases and minute particles). Severity of the airborne pollutants can vary by geographic location. Such pollutants may be most prevalent in geographical locations that include industrial regions. In addition, growing use of cooling systems in data centers that rely on bringing air from a nearby environment into the data center can increase the likelihood of bringing airborne pollutants into the data center. The structure of the data center (e.g., doors, windows, construction, relocations, and other variations) can also lead to an increase in airborne pollutants, and can create non-uniform air rates within a data center.

Currently, stationary chemical-based filters can be used to mitigate gaseous contaminations within data centers. The stationary chemical-based filters may have limitations (e.g., reacting to changing sources of contamination). Changing sources of the airborne pollutants may require manual effort to relocate the chemical filter to the source of contamination (e.g., relocating the filter from near a window to near a door). The stationary chemical based filter limitations may not be capable of prioritizing contaminations. For example, identifying a largest contamination out of one or more contaminations. This prioritizing can be useful for utilizing available filters or identifying filters that could be effective for counteracting the contamination. Furthermore, stationary filters may not have the ability to turn off unneeded filtration, which may result in wasted resources. Additionally, stationary filters may be unable to call for additional filters when needed. As such, it may be advantageous, among other things, to implement an automated robotic filtration program within data centers.

According to at least one embodiment, a robotic filtration program can be designed for filtering pollutants and gaseous contaminations within data centers as the pollutants and gaseous contaminations arise. Air pollutants and gaseous contaminations may be referred herein as airborne pollutants, air contaminations, particulates, or gaseous particulates. Consequently, pollutants and gaseous contaminations may be filtered within the contaminated zone. Furthermore, the robotic filtration program can analyze the air contamination level and respond to a high contamination level by relocating to a contaminated zone to filter particulate/gaseous particles.

Aspects of the present embodiment can utilize an automated system (e.g., MMT) designed to evaluate an environment (e.g. air quality) of a data center. Evaluation of the air quality can be achieved by mounting a chemical filter to the automated system. This mounting can enable the chemical filter to move freely about the data center. The automated system can then visually depict, in three dimensions, air quality distributions within a data center. The automated system can further rely on stationary sensors distributed throughout the data center. The stationary sensors can be mounted to one or more hardware racks within the data center. The stationary sensors can monitor the air quality by collecting air data and transmitting the collected air data to the automated system. Air data can include air samples within a nearby proximity to the sensor, such as within a zone.

The data center can be organized into one or more zones. Each zone can include one or more stationary sensors. The air data can be utilized to update a visual depiction of the air quality within the data center. The updated visual depiction can be transmitted for display within an UI. The UI can be within a client device (e.g., a cellular phone or a desktop computer). The automated system can deploy robotic filters to purify the air (i.e. remove airborne pollutants) within a zone near the sensors in response to the air data satisfying a threshold. In one embodiment, a plurality of robotic filters can be deployed in a single data center to purify contaminated air. The automated system can determine a robotic filter available and near the zone. Furthermore, the automated system can determine the shortest distance from the available, nearby robotic filter to the contaminated zone. The automated system can then instruct the robotic filter to filter the zone.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the various embodiments. As used herein, the singular forms "a," "an," and "the" are intended to include the plural forms as well, unless the context clearly indicates otherwise. It will be further understood that the terms "includes" and/or "including," when used in this specification, specify the presence of the stated features, integers, steps, operations, elements, and/or components, but do not preclude the presence or addition of one or more other features, integers, steps, operations, elements, components, and/or groups thereof. In the foregoing detailed description of exemplary embodiments of the various embodiments, reference was made to the accompanying drawings (where like numbers represent like elements), which form a part hereof, and in which is shown by way of illustration specific exemplary embodiments in which the various embodiments may be practiced. These embodiments were described in sufficient detail to enable those skilled in the art to practice the embodiments, but other embodiments may be used and logical, mechanical, electrical, and other changes may be made without departing from the scope of the various embodiments. In the foregoing description, numerous specific details were set forth to provide a thorough understanding the various embodiments. But, the various embodiments may be practiced without these specific details. In other instances, well-known circuits, structures, and techniques have not been shown in detail in order not to obscure embodiments.

Different instances of the word "embodiment" as used within this specification do not necessarily refer to the same embodiment, but they may. Any data and data structures illustrated or described herein are examples only, and in other embodiments, different amounts of data, types of data, fields, numbers and types of fields, field names, numbers and types of rows, records, entries, or organizations of data may be used. In addition, any data may be combined with logic, so that a separate data structure may not be necessary. The previous detailed description is, therefore, not to be taken in a limiting sense.

The following described exemplary embodiments provide a system, method, and program product to dynamically increase air quality within a data center via a mobile automated system upon air data satisfying a threshold. The mobile automated system may implement a response to a threshold being satisfied in the form of a robotic filter relocating to an area of contamination and filtering the contaminated area.

Referring to FIG. 1, an exemplary networked computer environment 100 is depicted, in accordance with one embodiment. The networked computer environment 100 may include a client computing device 110 and a server 120 interconnected via a communication network 130. According to at least one implementation, the networked computer environment 100 may include a plurality of client computing devices 110 and servers 120, only one of each being shown for illustrative brevity.

The communication network 130 may include various types of communication networks, such as a wide area network (WAN), local area network (LAN), a telecommunication network, a wireless network, a public switched network and/or a satellite network. The communication network 130 may include connections, such as wire, wireless communication links, or fiber optic cables. It may be appreciated that FIG. 1 provides only an illustration of one implementation and does not imply any limitations with regard to the environments in which different embodiments may be implemented. Many modifications to the depicted environments may be made based on design and implementation requirements.

The client computing device 110 may include a processor 104 and a data storage device 106 that is enabled to host a software program 108, an automated robotic filtration program 112A, and may communicate with the server 120 via the communication network 130, in accordance with one embodiment of the invention. The client computing device 110 may be, for example, a mobile device, a telephone, a personal digital assistant, a netbook, a laptop computer, a tablet computer, a desktop computer, a robotic filter, or any type of computing device capable of running a program and accessing a network. As will be discussed with reference to FIG. 8, the client computing device 110 may include internal components 802a and external components 804a, respectively.

The server computer 120 may be a laptop computer, netbook computer, personal computer (PC), a desktop computer, or any programmable electronic device capable of hosting an automated robotic filtration program 112B and communicating with the client computing device 110 via the communication network 130, in accordance with embodiments of the invention. As will be discussed with reference to FIG. 8, the server computer 120 may include internal components 802b and external components 804b, respectively. The server 120 may also operate in a cloud computing service model, such as Software as a Service (SaaS), Platform as a Service (PaaS), or Infrastructure as a Service (IaaS). The server 120 may also be located in a cloud computing deployment model, such as a private cloud, community cloud, public cloud, or hybrid cloud.

According to the present embodiment, the automated robotic filtration program 112A, 112B may be a program capable of receiving air data collected by the client device 110 from the processor 104, determining that the air data satisfies a threshold by the software program 108, transmitting a geographic location of a zone to the robotic filter by the software program 108, and dispatching a robotic filter to the geographic location to filter the air. The automated robotic filtration program 112A, 112B is explained in further detail below with respect to FIGS. 2-7.

Figure 2:
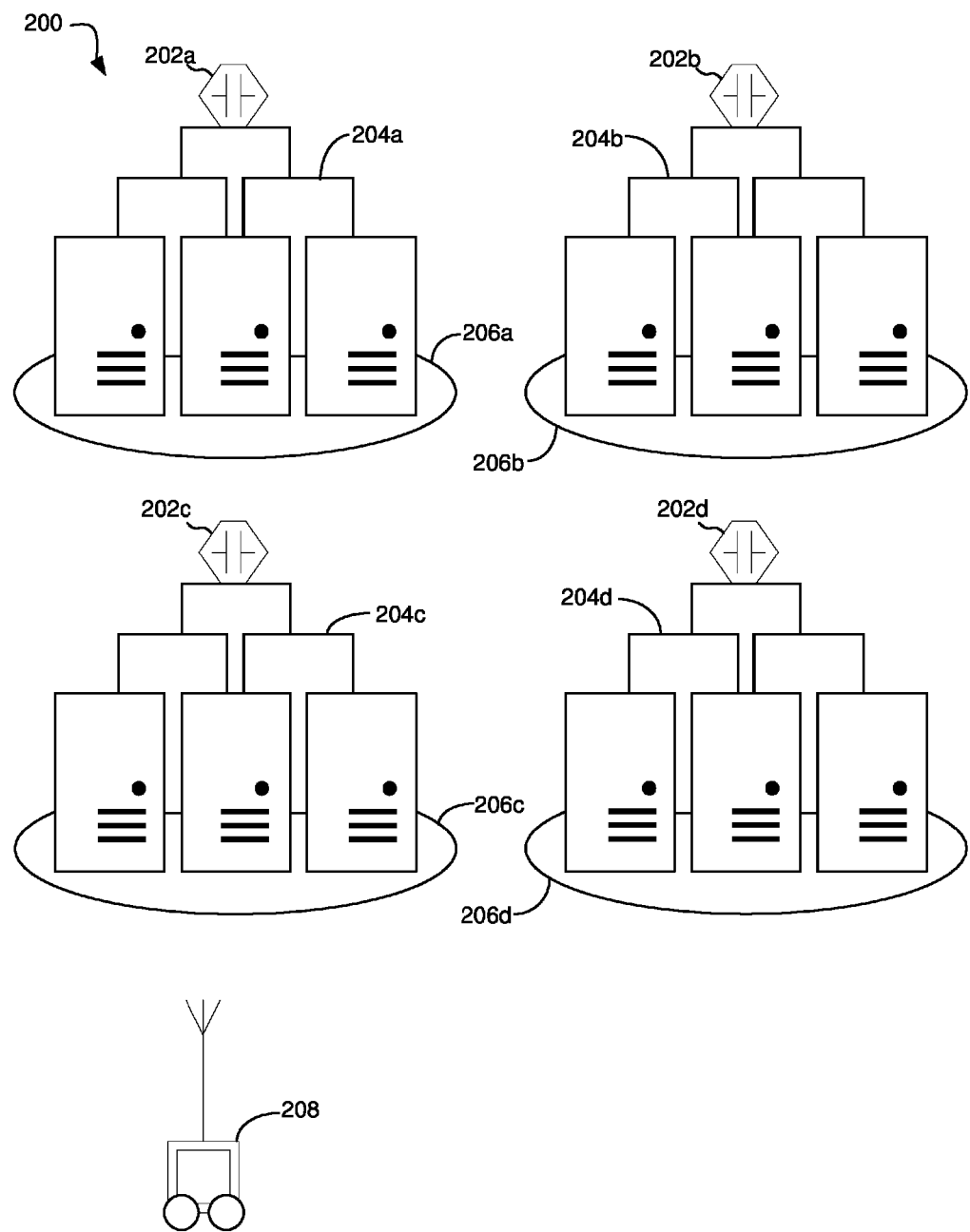
FIG. 2 illustrates an example of a data center where an embodiment of the present disclosure can be utilized, according to various embodiments.

Referring now to FIG. 2, an example data center 200 where an embodiment of the present disclosure can be utilized is depicted, according to various embodiments. The example data center 200 may include one or more zones (e.g., zones 206a-d) and a robotic filter 208. Each zone can include one or more hardware racks (e.g., hardware racks 204a-d) and one or more sensors (e.g., sensors 202a-d). Each of the sensors 202a-d may be capable of monitoring airborne pollution within a nearby proximity of the sensors 202a-d (i.e., their respective zones 206a-d). Additionally, the airborne pollution being monitored can include particles, humidity, gas leaks (e.g., high nitrous dioxide and carbon oxide concentrations), temperature, atmospheric pressure, radiation, pesticides, combustion emissions, and other environmental conditions that are capable of damaging computer hardware components. The sensors 202a-d can include instruments, such as particle counters, Geiger counters, thermometers, and barometers. Furthermore, the sensors 202a-d can collect air data within a nearby proximity and determine when the air data satisfies a threshold. The threshold may be a numerical representation (e.g., parts per million per volume) indicating the limit of an acceptable difference between the collected air pollutant and an approved quantity of the air pollutant. The magnitude of a particular air pollutant can have units that are relevant to the air pollutant (e.g. units of mmHg for atmospheric pressure). Satisfying the threshold may be accomplished when a magnitude of the collected airborne pollutant is more than the magnitude of the threshold. A threshold of a particular zone (e.g. zone 206a) can depend on hardware within the zone (e.g., zone 206a). For example, the threshold can be lowered when hardware within the zone 206a is highly susceptible to airborne pollutants.

Additionally, the automated robotic filtration program 112A, 112B (FIG. 1) can update a visual depiction of the air distribution in real time within the data center 200 based on the collected air data. The updated visual depiction can be displayed within an UI of a client device 110 (FIG. 1) such as, a smart phone, tablet, laptop, or desktop. The automated robotic filtration program 112A, 112B (FIG. 1) can further communicate with the robotic filter 208 for a particular zone (e.g., zone 206a) that the zone (e.g., zone 206a) needs to be filtered. This communication can occur in response to the threshold being satisfied.

In embodiments, the sensors 202a-d can be communicatively coupled to the robotic filter 208. The robotic filter 208 can respond to a communication from the sensors 202a-d by relocating to the zone (e.g., 206a) where filtration is needed. The robotic filter 208 can utilize a filter corresponding to a particular airborne pollutant. For example, the robotic filter 208 can utilize a chemical filter when a high density of a particular chemical pollutant satisfies the threshold. In other embodiments, one or more robotic filters 208 can be deployed to filter a particular zone (e.g., zone 206a) when there is a high level of an airborne pollutant. For example, one or more other robotic filters 208 can relocate to the zone 206a to filter air. A method for one or more robotic filters 208 relocating to a particular zone (e.g., 206a) in response to satisfying a threshold is discussed in reference to FIG. 3.

Figure 3:
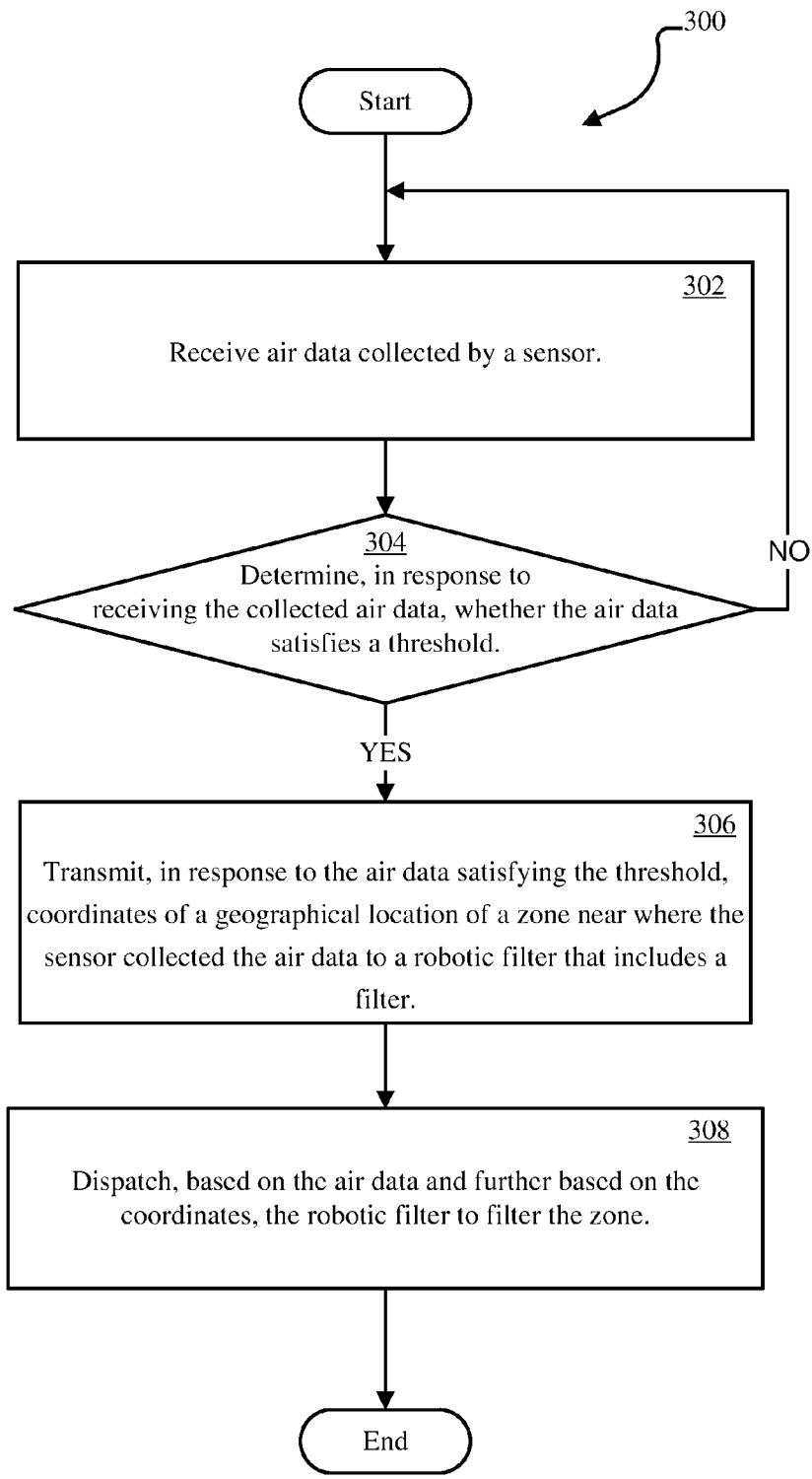
FIG. 3 illustrates an automated data center filtration system flowchart of a method for instructing a robotic filter to filter a data center, according to various embodiments.

Referring now to FIG. 3, an automated data center filtration program flowchart 300 of a method for instructing a robotic filter 208 (FIG. 2) to filter a data center 200 (FIG. 2) is depicted, according to various embodiments. At 302, the automated robotic filtration program 112A, 112B (FIG. 1) receives air data collected by a sensor (e.g., sensors 202a-d (FIG. 2)). As previously described, air data can include airborne pollutants (e.g. particles, humidity), gas leaks (e.g., high nitrous dioxide and carbon oxide concentrations), temperature, atmospheric pressure, radiation, combustion emissions, and other environmental conditions that are capable of damaging computer hardware (e.g., computer hardware rack 204a (FIG. 2)) within a zone (e.g., zone 206a (FIG. 2)), such as, within a nearby proximity of the sensor 202a (FIG. 2). The sensors 202a-d (FIG. 2) can include instruments, such as particle counters, Geiger counters, thermometers, and barometers. The air data can be received in the form of numerical data representing the quantities of each type of airborne pollutant in associated units. For example, temperature can be measured in units of Kelvin. Furthermore, the sensors 202a-d (FIG. 2) can continually collect air samples in incremented time intervals (e.g., every five minutes or every hour). The sensors 202a-d (FIG. 2) can be located throughout the data center. For example, the sensors 202a-d (FIG. 2) can be located on computer hardware racks 204a-b (FIG. 2) or integrated into the computer hardware racks 204a-b (FIG. 2).

Next, at 304, the automated robotic filtration program 112A, 112B (FIG. 1) determines whether the air data satisfies a threshold. According to one implementation, the method may continue along the automated data center filtration flowchart 300, if the air data satisfies a threshold. If the automated robotic filtration program 112A, 112B (FIG. 1) determines the air data satisfies a threshold (step 304, "YES" branch), the automated robotic filtration program 112A, 112B (FIG. 1) may continue to transmit coordinates to a robotic filter 208 (FIG. 2) that includes a filter at step 306. If the automated robotic filtration program 112A, 112B (FIG. 1) determines the air data does not satisfy a threshold (step 304, "NO" branch), the automated data center filtration flowchart 300 of the method may return to step 302 to receive air data collected by the sensors 202a-d (FIG. 2).

Determining whether the air data satisfies a threshold can be made in response to receiving the air data collected by the sensors 202a-d (FIG. 2). The threshold may be a numerical representation indicating the limit of an acceptable difference between the collected air contaminants and an approved quantity of the air contaminants. Satisfying the threshold may be accomplished when a magnitude of the collected airborne pollutant is more than the magnitude of the threshold. Each pollutant can have a different acceptable difference. The acceptable difference can depend on the airborne pollutants (e.g. chemical gases and dust) effect on hardware within a zone. For example, an increase of chemical gases and dust in the air can damage the hardware more than an increase of other environmental conditions (e.g. radioactivity). When the automated robotic filtration program 112A, 112B (FIG. 1) determines that the air data does satisfy the threshold, the automated data center filtration flowchart can continue to 306.

Then, at 306, the automated robotic filtration program 112A, 112B (FIG. 1) transmits coordinates to a robotic filter 208 (FIG. 2) that includes a filter. The transmitted coordinates may correspond to a geographical location within a zone (e.g., 206a (FIG. 2)) adjacent to where the sensors 202a-d (FIG. 2) collected the air data. The transmission can be in response to the air data satisfying the threshold at step 304. In some cases, the geographic location of a zone (e.g., 206a (FIG. 2)) can include an orientation for the robotic filter 208 (FIG. 2) within the zone 206a (FIG. 2). For example, the orientation can include a direction for the robotic filter 208 (FIG. 2) to face in order to counteract a wind current. The wind current can be propagating from a hole in a window and/or around a door. In embodiments, the sensor 202a (FIG. 2) can be communicatively coupled to the robotic filter 208 (FIG. 2) located within the data center 200 (FIG. 2). In some cases, the robotic filter 208 (FIG. 2) may not be within the data center 200 (FIG. 2). For example, the robotic filter 208 (FIG. 2) can be located within another data center adjacent to the data center 200 (FIG. 2).

Next, at 308, the automated robotic filtration program 112A, 112B (FIG. 1) dispatches the robotic filter 208 (FIG. 2) to the geographic location of the zone (e.g., 206a) to filter air. This dispatching can be based on the air data collected in step 302. In some cases, the dispatching can include transmitting one or more paths from the robotic filter 208 (FIG. 2) to the zone (e.g., 206a (FIG. 2)). In some cases, the one or more paths can include a shortest distance path. In some cases, the robotic filter 208 (FIG. 2) can include one or more filters. Each of the one or more filters can be associated with the type of air pollutant. For example, a chemical filter can be associated with chemical gases. An air dehumidifier can be associated with an increase of humidity. In some cases, the robotic filter 208 (FIG. 2) can include an electric-based fan that could redirect air into a filter for more expeditious filtering. For example, an electric-based fan can redirect a chemical gas into a chemical filter.

Figure 4:
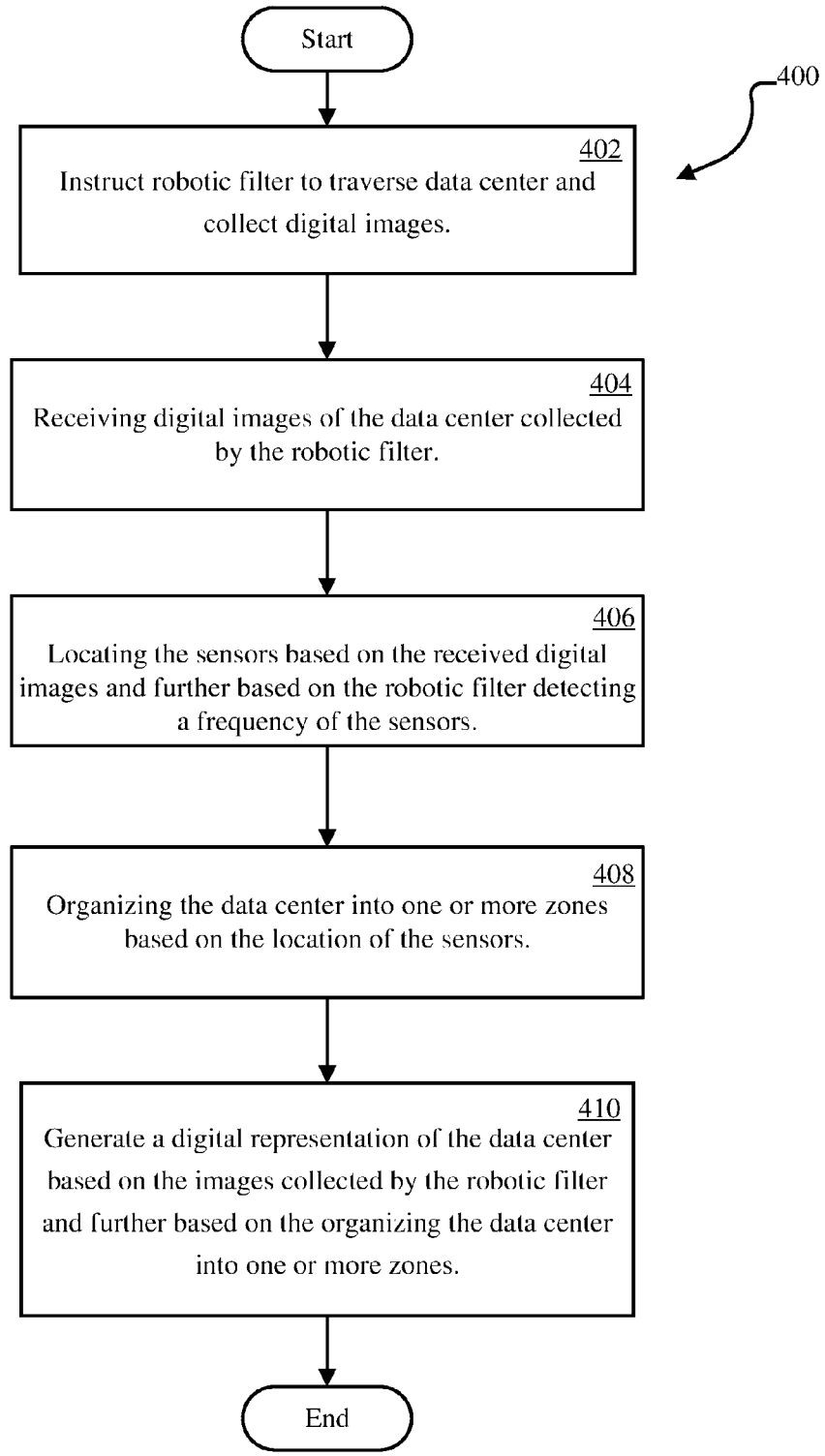
FIG. 4 illustrates a dynamic interactive digital representation generation flowchart of a method for generating a digital representation of a data center, according to various embodiments.

Referring now to FIG. 4, a dynamic interactive digital representation generation flowchart 400 of a method for generating a digital representation of a data center 200 (FIG. 2) is depicted, according to various embodiments. At 402, the automated robotic filtration program 112A, 112B (FIG. 1) instructs a robotic filter 208 (FIG. 2) to traverse the data center 200 (FIG. 2) and collect digital images of the data center 200 (FIG. 2). In some cases, collecting the digital images can be a first step of utilizing embodiments of the present disclosure within a data center 200 (FIG. 2). For example, the robotic filter 208 (FIG. 2) can traverse the data center 200 (FIG. 2) and collect digital images before any filtering begins.

Next, at 404, the automated robotic filtration program 112A, 112B (FIG. 1) receives the digital images of the data center 200 (FIG. 2) collected by the robotic filter 208 (FIG. 2) at step 402. In some cases, the digital images can be collected by electrical instruments (e.g., a digital camera). The digital camera can be integrated into or attached to the robotic filter 208 (FIG. 2). In some cases, aspects of the present disclosure can leverage existing technologies (e.g., MMT) to collect the digital images. The robotic filter 208 (FIG. 2) can identify the sensors 202a-d (FIG. 2) by detecting electromagnetic frequencies being emitted from the sensors 202a-d (FIG. 2). The sensors 202a-d (FIG. 2) can wirelessly emit frequencies within the electromagnetic spectrum (e.g., radio frequency). In some cases, the electromagnetic frequency can be emitted by radio frequency identification (RFID) devices that can be integrated into the sensors 202*a-d* (FIG. 2). The robotic filter 208 (FIG. 2) can then detect frequencies emitted by the RFID.

Then, at 406, the automated robotic filtration program 112A, 112B (FIG. 1) locates the sensors 202*a-d* (FIG. 2) within the data center 200 (FIG. 2). Locating the sensors 202*a-d* (FIG. 2) can be based on the digital images received at step 404. Furthermore, locating the sensors 202*a-d* (FIG. 2) can be based on the robotic filter 208 (FIG. 2) detecting a frequency emitted by the sensors 202*a-d* (FIG. 2) at step 404. Locating the sensors 202*a-d* (FIG. 2) based on the received digital images can be accomplished by performing known image analysis methods. The known image analysis methods can extract meaningful information from within the received digital images to be utilized by the robotic filter 208 (FIG. 2). Moreover, the known image analysis methods can be used for creating a visual representation of the data center 200 (FIG. 2) in the form of a map. Additionally, the known image analysis methods can identify the location of hardware racks 204*a-d* (FIG. 2) within the data center 200 (FIG. 2), as well as formulate a topological layout of the data center 200 (FIG. 2). This digital representation can be useful for determining a shortest distance from the robotic filter 208 (FIG. 2) to a zone (e.g., 206*a* (FIG. 2)), as described in step 308 (FIG. 3).

Next, at 408, the automated robotic filtration program 112A, 112B (FIG. 1) organizes the data center 200 (FIG. 2) into one or more zones 206*a-d* (FIG. 2). Organizing the data center 200 (FIG. 2) into one or more zones 206*a-d* (FIG. 2) can be based on the location of the sensors 202*a-d* (FIG. 2), described at step 406. In some cases, the one or more zones 206*a-d* (FIG. 2) can be based on the geographical locations of the sensors 202*a-d* (FIG. 2) within the data center 200 (FIG. 2). Each of the zones 206*a-d* (FIG. 2) can be included within a proximity of any one of the sensors 202*a-d* (FIG. 2). For example, any one of the zones 206*a-d* (FIG. 2) can be within a range of five feet from any one of the sensors 202*a-d* (FIG. 2). The zones 206*a-d* (FIG. 2) can be determined based on increasing the accuracy of the sensor (e.g., 202*a* (FIG. 2)) collecting air data. For example, the zone 206*a* (FIG. 2) including the sensor 202*a* (FIG. 2) can encompass more space when the sensor 202*a* (FIG. 2) is located near a door or a window, due to a possible crack in the window and/or door.

Next, at 410, the automated robotic filtration program 112A, 112B (FIG. 1) generates a digital representation of the data center 200 (FIG. 2). The digital representation can be based on the digital images collected by the robotic filter 208 (FIG. 2) at step 402. Furthermore, the digital representation can be based on organizing the data center 200 (FIG. 2) into the one or more zones 206*a-d* (FIG. 2) in step 408. The digital representation can be in the form of a map. The map can be interactive and can include at timestamp of when air data is collected. Additionally, the map can include a visual representation of the air pollutants in real time. For example, as the air data is collected within the data center 200 (FIG. 2), the map can be updated by the sensors 202*a-d* (FIG. 2) to include a visual representation of the air quality. For example, the updated visual representation can include when carbon monoxide is detected within a zone (e.g., zone 206*a* (FIG. 2)) and can then depict the carbon monoxide within the digital representation in a particular color. In some cases, the interactive map can be displayed within a UI of a client device 110 (FIG. 1) such as, a smart phone. This can be useful when monitoring the air data collected externally to the data center 200 (FIG. 2).

Figure 5:
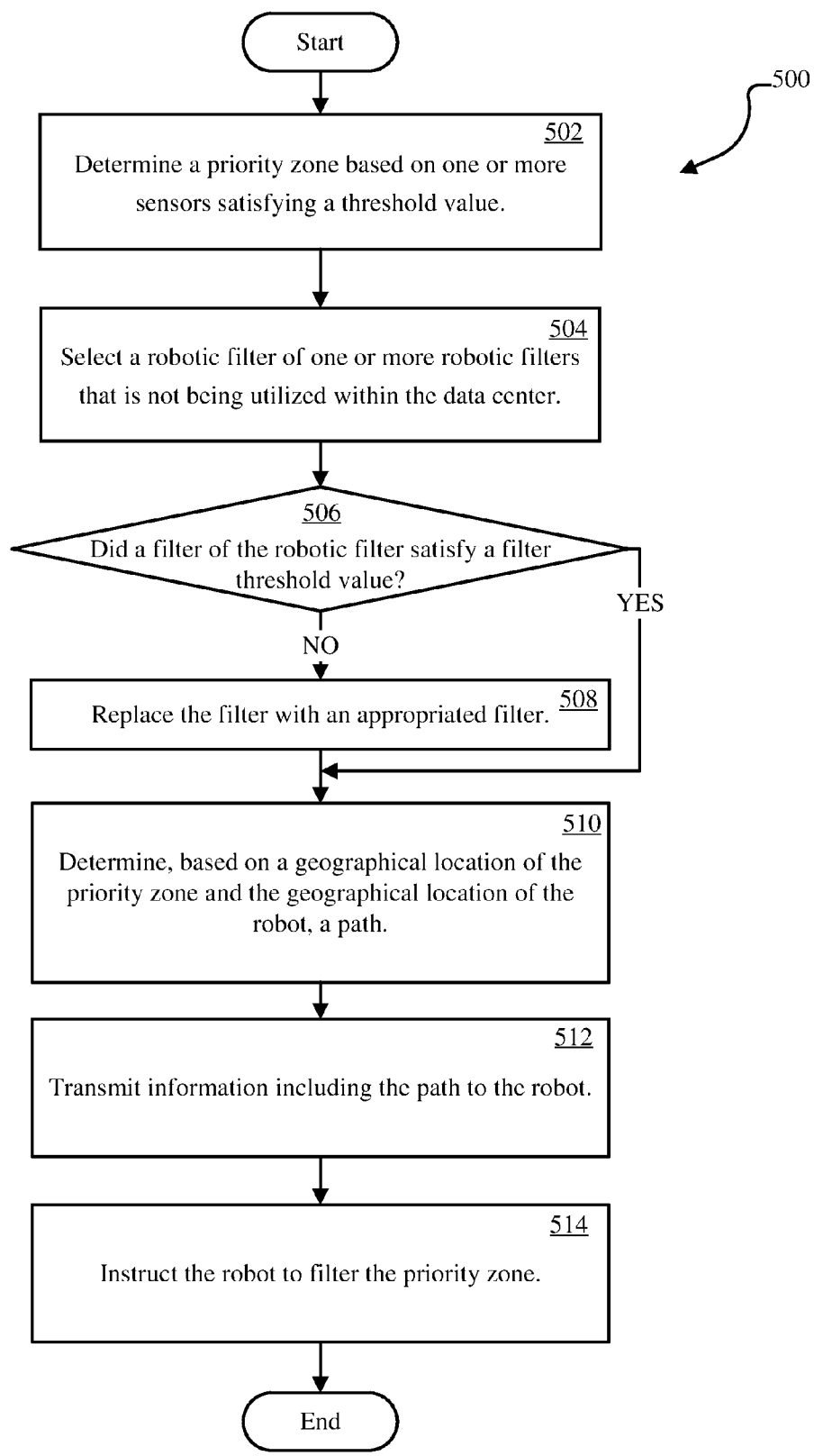
FIG. 5 illustrates a robotic filter priority flowchart of a method for designating a robotic filter of one or more robotic filters to filter a priority zone, according to various embodiments.

Referring now to FIG. 5, a robotic filter priority flowchart 500 of a method for designating a robotic filter 208 (FIG. 2) of one or more robotic filters 208 (FIG. 2) to filter a priority zone is depicted, according to various embodiments. At 502, the automated robotic filtration program 112A, 112B (FIG. 1) determines a priority zone (e.g., zone 206*a* (FIG. 2)) based on one or more sensors 202*a-d* (FIG. 2) satisfying a threshold value. In some cases, the priority zone (e.g., zone 206*a* (FIG. 2)) can be any one of the one or more zones 206*a-d* (FIG. 2). The priority zone (e.g., zone 206*a* (FIG. 2)) can be determined based on having contaminations of one or more airborne pollutants within a proximity. For example, a determination could be based on the priority zone (e.g., zone 206*a* (FIG. 2)) including more carbon dioxide or other chemical gases than other zones 206*b-d* (FIG. 2) within the data center 200 (FIG. 2). As an additional example, the determination could be based on the priority zone (e.g., 206*a* (FIG. 2)) including a combination of pollutants (e.g. chemical gases and minute particles) which could potentially damage hardware within the priority zone (e.g., 206*a* (FIG. 2)) at a quicker rate than other hardware included within other zones 206*b-d* (FIG. 2) within the data center 200 (FIG. 2).

Then, at 504, the automated robotic filtration program 112A, 112B (FIG. 1) selects a robotic filter (e.g., robotic filter 208 (FIG. 2)) of one or more robotic filters 208 (FIG. 2) that is not being utilized within the data center. When all robotic filters 208 (FIG. 2) within the data center 200 (FIG. 2) are currently being utilized, a robotic filter 208 (FIG. 2) could be identified based on the time of completion of the current filtering. For example, a robotic filter 208 (FIG. 2) may be identified based on the robotic filter 208 (FIG. 2) finishing filtering a zone (e.g., zone 206*a* (FIG. 2)) in three minutes, whereas all other robotic filters 208 (FIG. 2) will be finished in more than five minutes.

Next, at 506, the automated robotic filtration program 112A, 112B (FIG. 1) determines whether the filter of the robotic filter 208 (FIG. 2) satisfies a filter threshold value. The filter not satisfying the filter threshold value can mean that the filter may not be effective in filtering the zone (e.g., zone 206*a* (FIG. 2)) such as, a clogged filter. The filter may not satisfy the threshold when the current filter type may not be a correct filter type. For example, the current filter can be designed to filter chemical gases and may need to be replaced with a minute particle filter to effectively filter the zone 206*a* (FIG. 2). According to one implementation, the robotic filter priority flowchart 500 of a method may continue to 510 when the automated robotic filtration program 112A, 112B (FIG. 1) determines that the filter satisfies the filter threshold value. If the automated robotic filtration program 112A, 112B (FIG. 1) determines that the filter does not satisfy the filter threshold, the automated robotic filtration program 112A, 112B (FIG. 1) can continue to 508.

Then, at 508, the automated robotic filtration program 112A, 112B (FIG. 1) replaces the filter with an appropriate filter. The appropriate filter can be any filter that can be effective for filtering the airborne pollutant that satisfied the threshold value at step 502. For example, if a chemical gas is the airborne pollutant that satisfied the threshold value, then the appropriate filter may be a filter designed to purify air from chemical gases. Additionally, the appropriate filter can also be the same type of filter that failed to satisfy the filter threshold value due to being clogged. For example, the appropriate filter can be a new filter that is not clogged.

However, if it is determined that the filter does satisfy the filter threshold value at 506, or if the automated robotic filtration program 112A, 112B (FIG. 1) replaced the filter at 508, then the automated robotic filtration program 112A, 112B (FIG. 1) determines a path at 510. The path can be based on a geographical location of the priority zone (e.g., zone 206a (FIG. 2)) and the geographical location of the robotic filter 208 (FIG. 2). The path can be starting from the robotic filter 208 (FIG. 2) and ending at a geographic location near or within the zone (e.g., zone 206a (FIG. 2)). In some cases, the path can be the shortest distance from the robotic filter 208 (FIG. 2) to the zone 206a (FIG. 2). Alternatively, the path can be determined based on where robotic filters 208 (FIG. 2) and other obstacles may be at given times. The path can be updated in increment timed intervals (e.g., every five seconds).

Then, at 512, the automated robotic filtration program 112A, 112B (FIG. 1) transmits the path to the robotic filter 208 (FIG. 2). In some cases, the path can be stored when the robotic filter 208 (FIG. 2) is currently filtering a zone (e.g., zones 206b-d (FIG. 2)), as opposed to the priority zone (e.g., zone 206a (FIG. 2)). The path can be updated based on real-time information by the sensors 202a-d (FIG. 2). For example, if an obstacle is included in the robotic filter's 208 (FIG. 2) path that was not included in the initial path, then the robotic filter 208 (FIG. 2) can go around that obstacle.

Next, at 514, the automated robotic filtration program 112A, 112B (FIG. 1) instructs the robotic filter 208 (FIG. 2) to filter the priority zone (e.g., zone 206a (FIG. 2)). This instruction can be substantially similar to the instruction given to the robotic filter 208 (FIG. 2) at step 308 (FIG. 3). In some cases, the robotic filter 208 (FIG. 2) can be communicatively coupled with sensors 202a-d (FIG. 2) located externally to the data center 200 (FIG. 2) that can collect air data outside the data center 200 (FIG. 2). The external air data can be compared with air data collected within the data center 200 (FIG. 2), thereby increasing the likelihood of determining when airborne pollutants can enter the data center 200 (FIG. 2), and from where the airborne pollutants may enter. The robotic filter 208 (FIG. 2) can utilize this external information and respond to airborne pollutants before any of the sensors 202a-d (FIG. 2) satisfy the threshold value.

Figure 6:
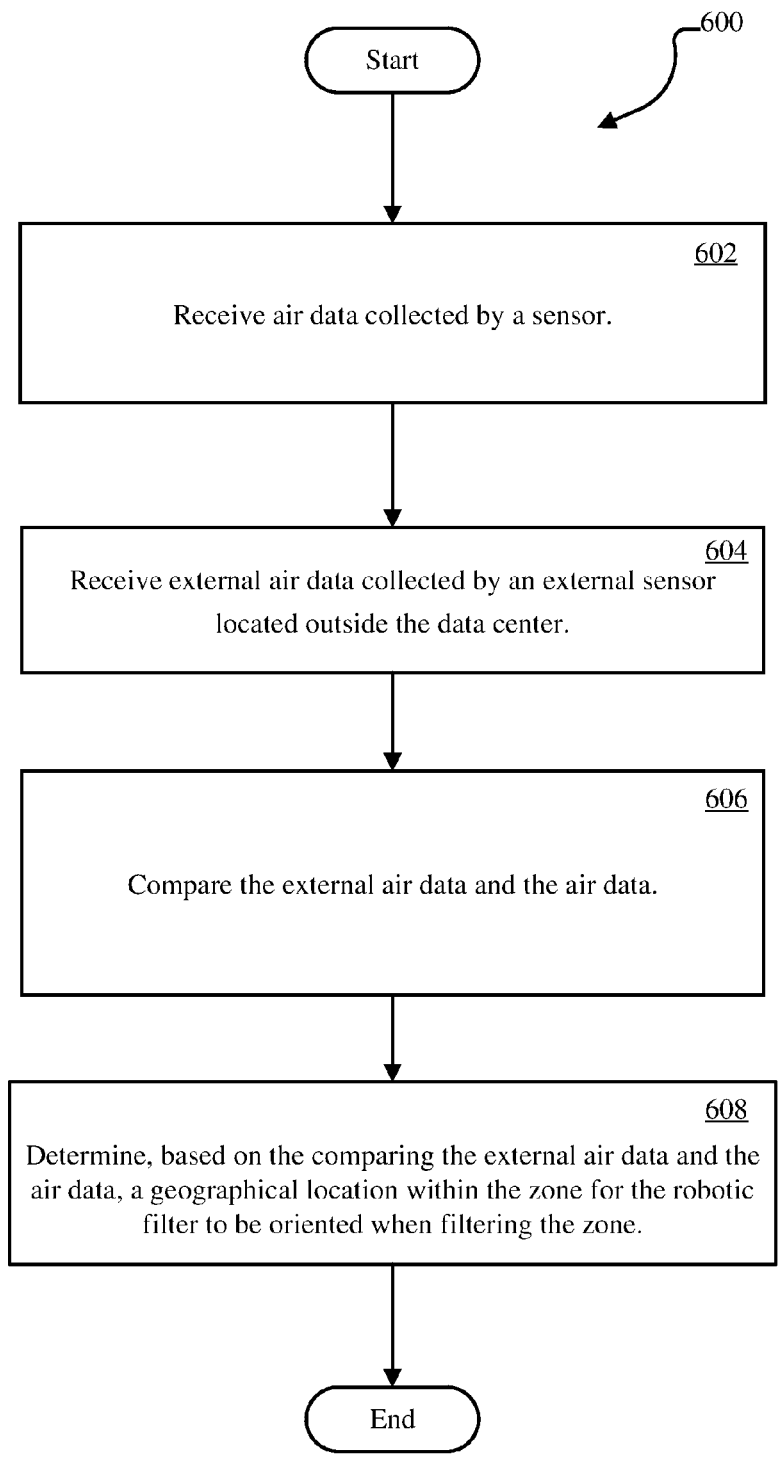
FIG. 6 illustrates a robotic filter orientation flowchart of a method for determining a geographical location within a zone for the robotic filter to be oriented while filtering the zone, according to various embodiments.

Referring now to FIG. 6, a robotic filter orientation flowchart 600 of a method for determining a geographical location within a zone (e.g., zone 206a (FIG. 2)) for the robotic filter 208 (FIG. 2) to be oriented when filtering the zone 206a (FIG. 2) is depicted, according to various embodiments. At 602, air data collected by a sensor (e.g., 202a (FIG. 2)) is received, substantially similar to the method at step 302 (FIG. 3). As previously described, air data can include airborne pollutants (e.g. particles, humidity), gas leaks (e.g., high nitrous dioxide and carbon oxide concentrations), temperature, atmospheric pressure, radiation, combustion emissions, and other environmental conditions that are capable of damaging computer hardware within a zone (e.g., 206a (FIG. 2)), such as, within a nearby proximity of the sensor (e.g., sensor 202a (FIG. 2)). The sensors 202a-d (FIG. 2) can include instruments, such as particle counters, Geiger counters, thermometers, and barometers. In embodiments, the sensors 202a-d (FIG. 2) can collect air data at regular time intervals (e.g., every five minutes or every hour).

Then, at 604, the automated robotic filtration program 112A, 112B (FIG. 1) receives external air data collected by an external sensor located outside the data center 200 (FIG. 2). In embodiments, the external sensors can include instruments, such as the sensors 202a-d (FIG. 2), collecting air data within the data center 200 (FIG. 2) at 602. In some cases, the external sensors can be stationary or mobile. The external sensors can be within a proximity of the data center 200 (FIG. 2). The stationary sensors can be at fixed locations surrounding and within a range of the data center 200 (FIG. 2) such as, one hundred feet or one mile from the data center. Externally stationed sensors can track air pollutant distributions to determine potential effects of the air pollutants to the data center 200 (FIG. 2). Externally mobile sensors can traverse nearby (e.g. within twenty feet or fifty feet) of the data center 200 (FIG. 2). The external sensors can be located near sources of fresh air to the data center 200 (FIG. 2) such as, near where air is collected when the data center utilizes an air cooling system. Additionally, the mobile sensors can be relocated to potential leaks of air to the data center 200 (FIG. 2) such as, doors, windows, and the source of fresh air.

Next, at 606, the automated robotic filtration program 112A, 112B (FIG. 1) compares the external air data to the air data. This comparison can be advantageous for predicting an increase of air pollutants within the data center 200 (FIG. 2) and can provide an opportunity to prepare for a predicted increase in air pollutants. In some cases, the air data can be compared to a source of fresh air. This can be advantageous for counteracting airborne pollutants that might be pumped into the data center 200 (FIG. 2) by a cooling system.

Then, at 608, the automated robotic filtration program 112A, 112B (FIG. 1) determines a geographical location within the zone 206a (FIG. 2) for the robotic filter 208 (FIG. 2) to filter based on the comparison of the external air data and the air data at 606. In some embodiments, the one or more robotic filters 208 (FIG. 2) can include chemical filters along with light weight electric-based fans. The electric-based fans can redirect airflow to the chemical filter based on the comparison made at step 606. The redirection of airflow can increase the rate of filtering air. For example, a prediction can be made that there will be an increase of air pollutants near a door of the data center 200 (FIG. 2). Robotic filters 208 (FIG. 2) can then be relocated to near the door and the electric-based fans can redirect the air pollutants into a chemical filter. This can increase the likelihood of filtering air entering the data center 200 (FIG. 2) before the air pollutants can affect hardware of the data center 200 (FIG. 2). In some cases, the direction of the flow of airborne pollutants can be determined. Determining a geographical location within the zone 206a (FIG. 2) to place the filter to increase the rate of filtering the data center 200 (FIG. 2) can be made based on the flow of air pollutants. Filtration of the air can be increased by positioning the electric-based fan such that the air pollutant can be redirected into the filter. In some cases, one or more robotic filters 208 (FIG. 2) can be instructed to disperse throughout the data center 200 (FIG. 2) in response to fresh air being compared to the air data. In this case, the robotic filter 208 (FIG. 2) can be prepared when an air cooling system pumps airborne pollutants into the data center 200 (FIG. 2). Furthermore, the robotic filter 208 (FIG. 2) can begin filtering the data center 200 (FIG. 2) before the cooling system pumps the airborne pollutants into the data center 200 (FIG. 2).

A follow up example explaining embodiments of the present disclosure is included herein. Initially the robotic filter 208 (FIG. 2) explores the entire data center 200 (FIG. 2), as previously described at step 402 (FIG. 4), and generates a map of the data center 200 (FIG. 2) as previously described at step 410 (FIG. 4). A geographic location of the one or more sensors 202a-d (FIG. 2) are identified as previously discussed at step 406 (FIG. 4) and then saved. An automated robotic filtration program 112A, 112B (FIG. 1) can organize the data center 200 (FIG. 2) into zones 206a-d (FIG. 2) based on the geographic locations of the one or more sensors 202a-d (FIG. 2), as previously described at step 408 (FIG. 4). Any of the zones 206a-d (FIG. 2) can include one or more sensors 202a-d (FIG. 2). The automated robotic filtration program 112A, 112B (FIG. 1) can further prioritize the zones 206a-d (FIG. 2) based on real-time air data collected within each zone as previously described at step 502 (FIG. 5). A robotic filter 208 (FIG. 2) can relocate to a priority zone (e.g., zone 206a (FIG. 2)) when at least one threshold value is satisfied. Thereafter, the map of the data center 200 (FIG. 2) and a three-dimensional air quality distribution can be visually displayed within a UI on an electric device. The visual display can highlight problem areas and potential causes (e.g., leaks in a window or door), and then corrective action may be taken. The automated robotic filtration program 112A, 112B (FIG. 1) can analyze the air data periodically and may re-deploy the robotic filters 208 (FIG. 2) to another zone (e.g., zone 206b (FIG. 2)) based on real-time air data. The automated robotic filtration program 112A, 112B (FIG. 1) can then instruct the filter to be replaced, as described at step 508 (FIG. 5), and can further instruct the robotic filter 208 (FIG. 2) to return to the docking station when a threshold value is not satisfied. In some cases, the robotic filters 208 (FIG. 2) can be battery operated. The battery operated robotic filters 208 (FIG. 2) can recharge at a docking station when they are not being utilized.

Figure 7:
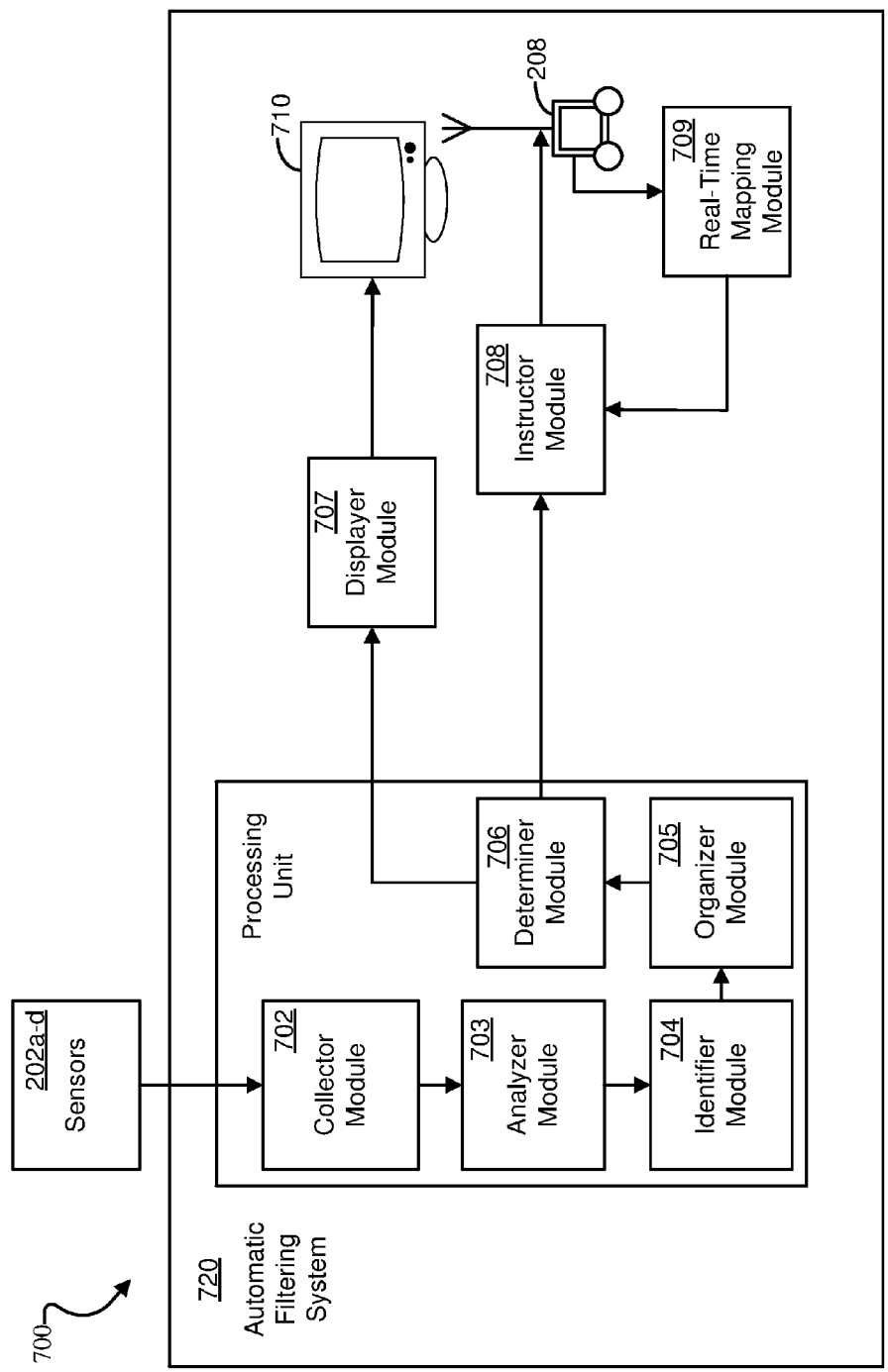
FIG. 7 is a block diagram depicting an exemplary system for automatically filtering a data center with robotic filters based on air data, according to various embodiments.

Referring to FIG. 7, a diagram of an example system 700 for automatically filtering a data center 200 (FIG. 2) with robotic filters 208 based on air data is depicted, according to various embodiments. In some embodiments, one or more sensors 202a-d can collect air data, as previously discussed at step 302 (FIG. 3), near one or more computer hardware racks 204a-d (FIG. 2) located within a data center 200 (FIG. 2) utilizing an automatic filtering system 720. The automatic filtering system 720 could include an aspect of the present disclosure integrated within its housing. The sensors 202a-d can include, but are not limited to, particle counters, Geiger counters, thermometers, and barometers. According to at least one embodiment, the sensors 202a-d can transmit the air data to a collector module 702 in the form of an electrical signal. According to at least one other embodiment, the collector module 702 can receive the air data, as previously discussed at step 302 (FIG. 3), in discrete time intervals. According to yet another embodiment, once the collector module 702 has received the air data from the sensors 202a-d, the sensors 202a-d can then transmit the electrical signal to an analyzer module 703. The analyzer module 703 can perform basic calculations and chemical analysis to decode the air data. For example, the analyzer module 703 can determine the air quality and airborne pollutants nearby the sensors 202a-d. Once the analyzer module 703 has analyzed the air data, the analyzer module 703 can transmit the analyzed air data to an identifier module 704.

The identifier module 704 can identify air pollutants that are within a proximity of the sensors 202a-d (i.e., within a zone (e.g., zone 206a (FIG. 2)) that includes the sensors 202a-d. The identifier 704 module can also identify chemical gases, dust, minute particles, and other airborne pollutants that can cause potential damage to computing devices. The identifier module 704 can relate the position of each of the airborne pollutants in real time. In some embodiments, once the identifier module 704 has identified airborne pollutants, the identifier module 704 can transmit an electrical signal that includes an analysis of the identified airborne pollutants to an organizer module 705.

The organizer module 705 can group one or more robotic filters 208 within the data center 200 (FIG. 2). For example, the available robotic filters 208 can be grouped together and the unavailable robotic filters 208 can be grouped together.

According to at least one embodiment, the organizer module 705 can further weigh each of the robotic filters 208 according to the position of the robotic filter 208 relative to the zone (e.g., zone 206a (FIG. 2)) that includes the airborne pollutants. For example, a robotic filter 208 located nearby the zone 206a (FIG. 2) might be weighted more heavily than a robotic filter 208 located far away from the zone 206a (FIG. 2). Once the organizer module 705 has grouped and weighted the robotic filters 208, the organizer module 705 can transmit that information to a determiner module 706 in the form of an electrical signal. According to at least one embodiment, the determiner module 706 can determine a robotic filter 208 based on the information that it has received. Then, the determiner module 706 can transmit the analyzed information to a displayer module 707, as well as an instructor module 708.

The displayer module 707 can generate a visual representation that can include three-dimensional airborne pollutant distributions within the data center 200 (FIG. 2), as previously discussed at step 410 (FIG. 4). The visual representation can be displayed within a UI. This generated UI can be substantially similar to the UI described in FIG. 4 and FIG. 5. For example, the UI can display within a screen 710 of the automatic filtering system 720. The one or more sensors 202a-d and robotic filters 208 can be indicated within the UI along with a display of the air data. According to at least one embodiment, the displayer module 707 can structure an image such that the visual representation fits to the screen 710 of the automatic filtering system. This structuring capability can fit to one or more UI screen sizes of different dimensions (e.g., a smart phone, a desktop computer, and a tablet).

The instructor module 708 can also receive the analyzed information that can include the robotic filter 208 determined to filter the zone 206a (FIG. 2) from the determiner module 706. The instructor module 708 can instruct the robotic filter 208 to filter the zone 206a (FIG. 2) as previously discussed at step 308 (FIG. 3). The instructor module 708 can instruct the robotic filter 208 to proceed along a path that the determiner module 706 generated based on the distance from the robotic filter 208 to the zone (e.g., zone 206a (FIG. 2)), as previously described at step 514 (FIG. 5). According to at least one embodiment, the user of the client device 110 (FIG. 1) can set a preferred path for the robotic filter 208 to traverse. According to at least one other embodiment, the instructor module 708 can adjust the path. According to yet another embodiment, the user can then manually instruct the robotic filter 208 used to filter the zone 206a (FIG. 2).

The robotic filter 208 can output its current position. According to at least one embodiment, the output can be connectively coupled with a real-time mapping module 709. The real-time mapping module 709 can monitor the position of the robotic filter 208 with respect to objects (e.g. other robotic filters 208 and computer hardware racks 204a-d (FIG. 2)) within the data center 200 (FIG. 2). The real-time mapping module 709 can determine the position of the robotic filter 208 within the data center 200 (FIG. 2) that the automatic filtering system 720 is operating in. The real-time mapping module 709 can transmit a value of the position of the robotic filter 208 in the form of an electrical signal to the instructor module 708. The instructor module 708 can then adjust the position of the robotic filter 208 based on the value of the outputted position of the robotic filter 208. According to at least one embodiment, this process can repeat continuously so that the current position of the robotic filter 208 is being adjusted based on the environment at a present time.

It may be appreciated that FIGS. 2-7 provide only an illustration of at least one embodiment but do not imply any limitations with regard to how different embodiments may be implemented. Many modifications to the depicted embodiment(s) may be made based on design and implementation requirements.

Figure 8:
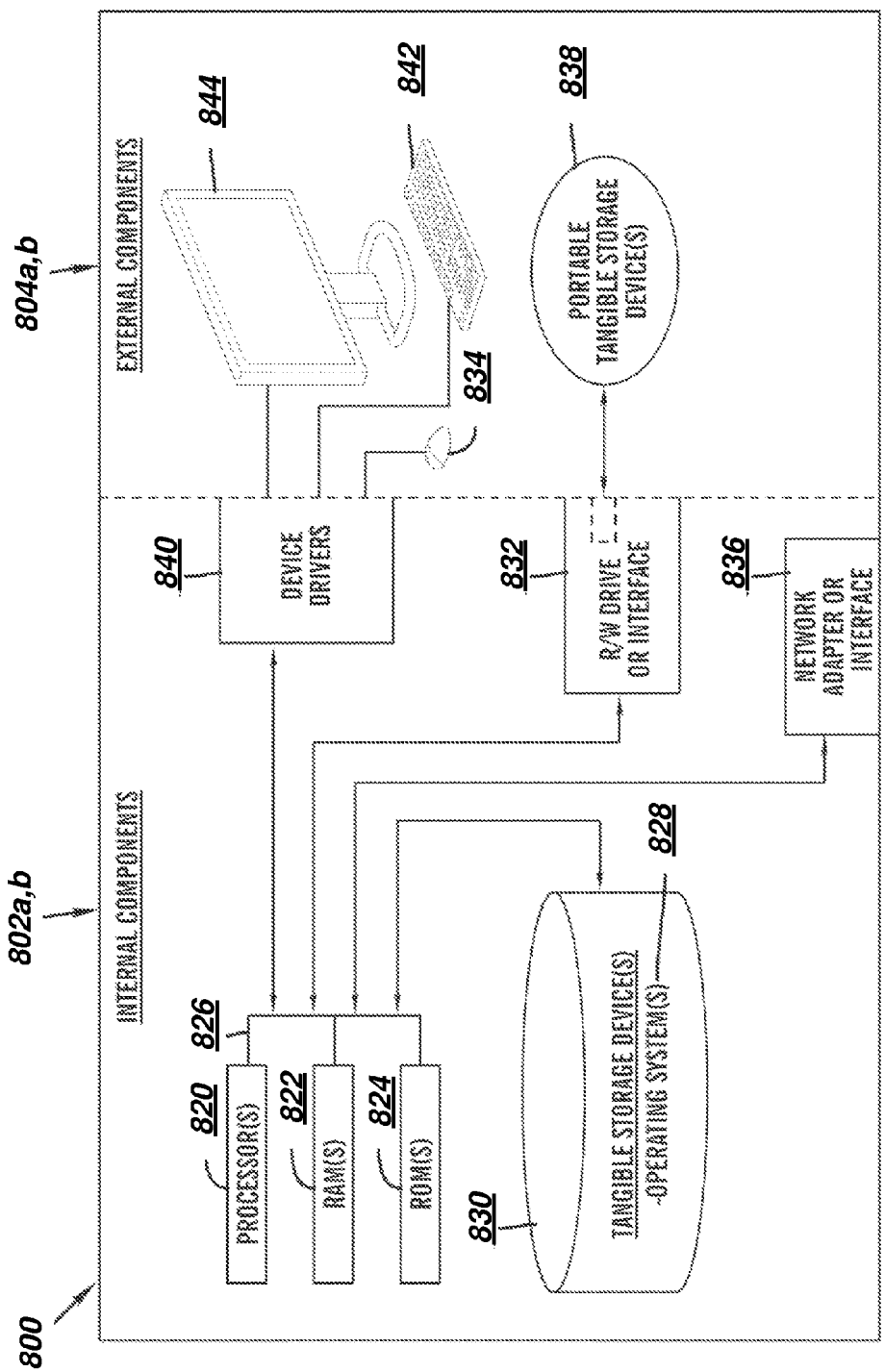
FIG. 8 is a block diagram of internal and external components of computers and servers depicted in FIG. 1 according to at least one embodiment.

In some embodiments, the operations and modules described herein can be included within and performed by components of a computer (e.g., a processor), such as the computer system described in FIG. 8.

FIG. 8 is a block diagram 800 of internal and external components of the client computing device 110 and the server 120 depicted in FIG. 1 in accordance with an embodiment of the present invention. It should be appreciated that FIG. 8 provides only an illustration of one implementation and does not imply any limitations with regard to the environments in which different embodiments may be implemented. Many modifications to the depicted environments may be made based on design and implementation requirements.

The data processing system 802, 804 is representative of any electronic device capable of executing machine-readable program instructions. The data processing system 802, 804 may be representative of a smart phone, a computer system, PDA, or other electronic devices. Examples of computing systems, environments, and/or configurations that may represented by the data processing system 802, 804 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

The client computing device 110 (FIG. 1) and the server 120 (FIG. 1) may include respective sets of internal components 802 a,b and external components 804 a,b illustrated in FIG. 8. Each of the sets of internal components 802 include one or more processors 820, one or more computer-readable RAMs 822, and one or more computer-readable ROMs 824 on one or more buses 826, and one or more operating systems 828 and one or more computer-readable tangible storage devices 830. The one or more operating systems 828, the automated robotic filtration program 112A (FIG. 1) in the client computing device 110 (FIG. 1), and the automated robotic filtration program 112B (FIG. 1) in the server 120 (FIG. 1) are stored on one or more of the respective computer-readable tangible storage devices 830 for execution by one or more of the respective processors 820 via one or more of the respective RAMs 822 (which typically include cache memory). In the embodiment illustrated in FIG. 8, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 802 a,b also includes a R/W drive or interface 832 to read from and write to one or more portable computer-readable tangible storage devices 838 such as a CD-ROM, DVD, memory stick, magnetic tape, magnetic disk, optical disk or semiconductor storage device. A software program, such as the automated robotic filtration program 112A, 112B (FIG. 1), can be stored on one or more of the respective portable computer-readable tangible storage devices 838, read via the respective R/W drive or interface 832 and loaded into the respective hard drive 830.

Each set of internal components 802 a,b also includes network adapters or interfaces 836 such as a TCP/IP adapter cards, wireless Wi-Fi interface cards, or 3G or 4G wireless interface cards or other wired or wireless communication links. The automated robotic filtration program 112A (FIG. 1) in the client computing device 110 (FIG. 1) and the automated robotic filtration program 112B (FIG. 1) in the server 120 (FIG. 1) can be downloaded to the client computing device 110 (FIG. 1) and the server 120 (FIG. 1) from an external computer via a network (for example, the Internet, a local area network or other, wide area network) and respective network adapters or interfaces 836. From the network adapters or interfaces 836, the automated robotic filtration program 112A (FIG. 1) in the client computing device 110 (FIG. 1) and the automated robotic filtration program 112B (FIG. 1) in the server 120 (FIG. 1) are loaded into the respective hard drive 830. The network may comprise copper wires, optical fibers, wireless transmission, routers, firewalls, switches, gateway computers and/or edge servers.

Each of the sets of external components 804 a,b can include a computer display monitor 844, a keyboard 842, and a computer mouse 834. External components 804 a,b can also include touch screens, virtual keyboards, touch pads, pointing devices, and other human interface devices. Each of the sets of internal components 802 a,b also includes device drivers 840 to interface to computer display monitor 844, keyboard 842, and computer mouse 834. The device drivers 840, R/W drive or interface 832, and network adapter or interface 836 comprise hardware and software (stored in storage device 830 and/or ROM 824).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 9:
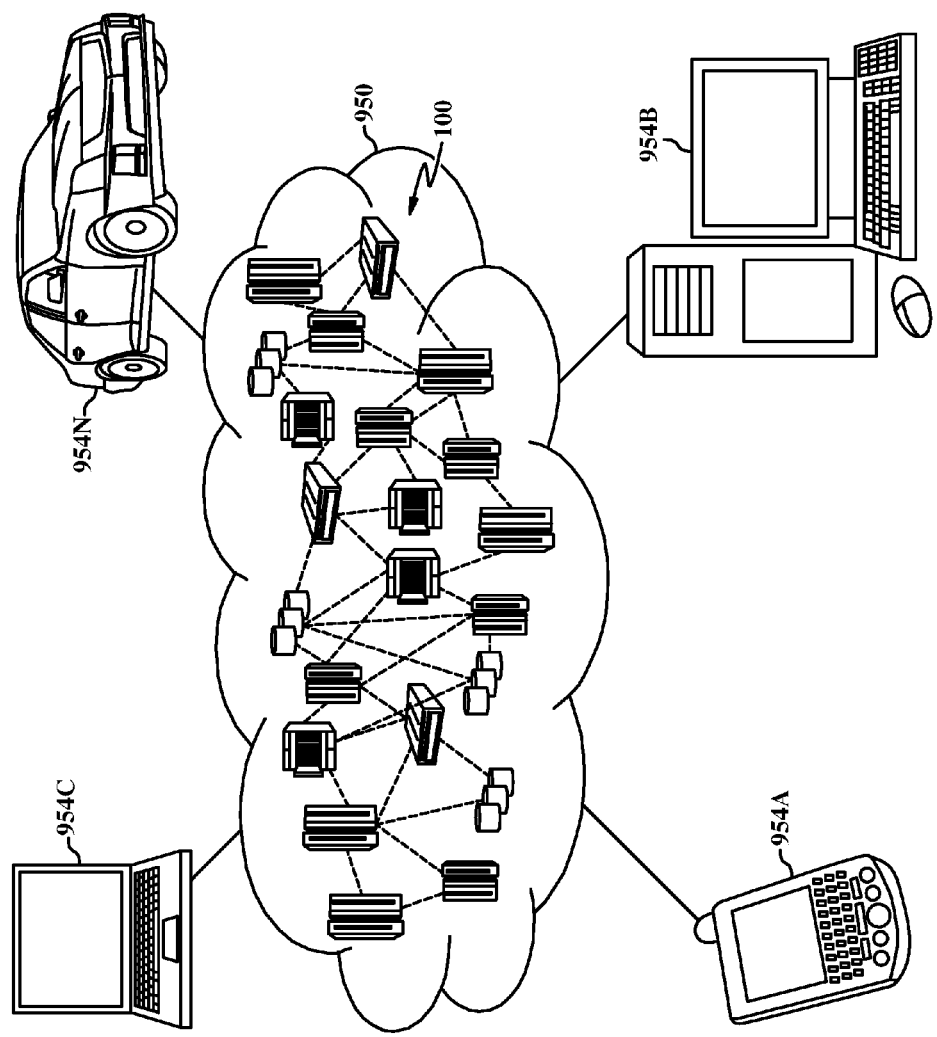
FIG. 9 is a block diagram of an illustrative cloud computing environment including the computer system depicted in FIG. 1, in accordance with an embodiment of the present disclosure.

Referring now to FIG. 9, illustrative cloud computing environment 950 is depicted. As shown, cloud computing environment 950 comprises one or more cloud computing nodes 100 with which local computing devices used by cloud consumers, such as, for example, personal digital assistant (PDA) or cellular telephone 954A, desktop computer 954B, laptop computer 954C, and/or automobile computer system 954N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 950 to offer infrastructure, platforms and/or software as services for which a cloud consumer does not need to maintain resources on a local computing device. It is understood that the types of computing devices 954A-N shown in FIG. 9 are intended to be illustrative only and that computing nodes 100 and cloud computing environment 950 can communicate with any type of computerized device over any type of network and/or network addressable connection (e.g., using a web browser).

Figure 10:
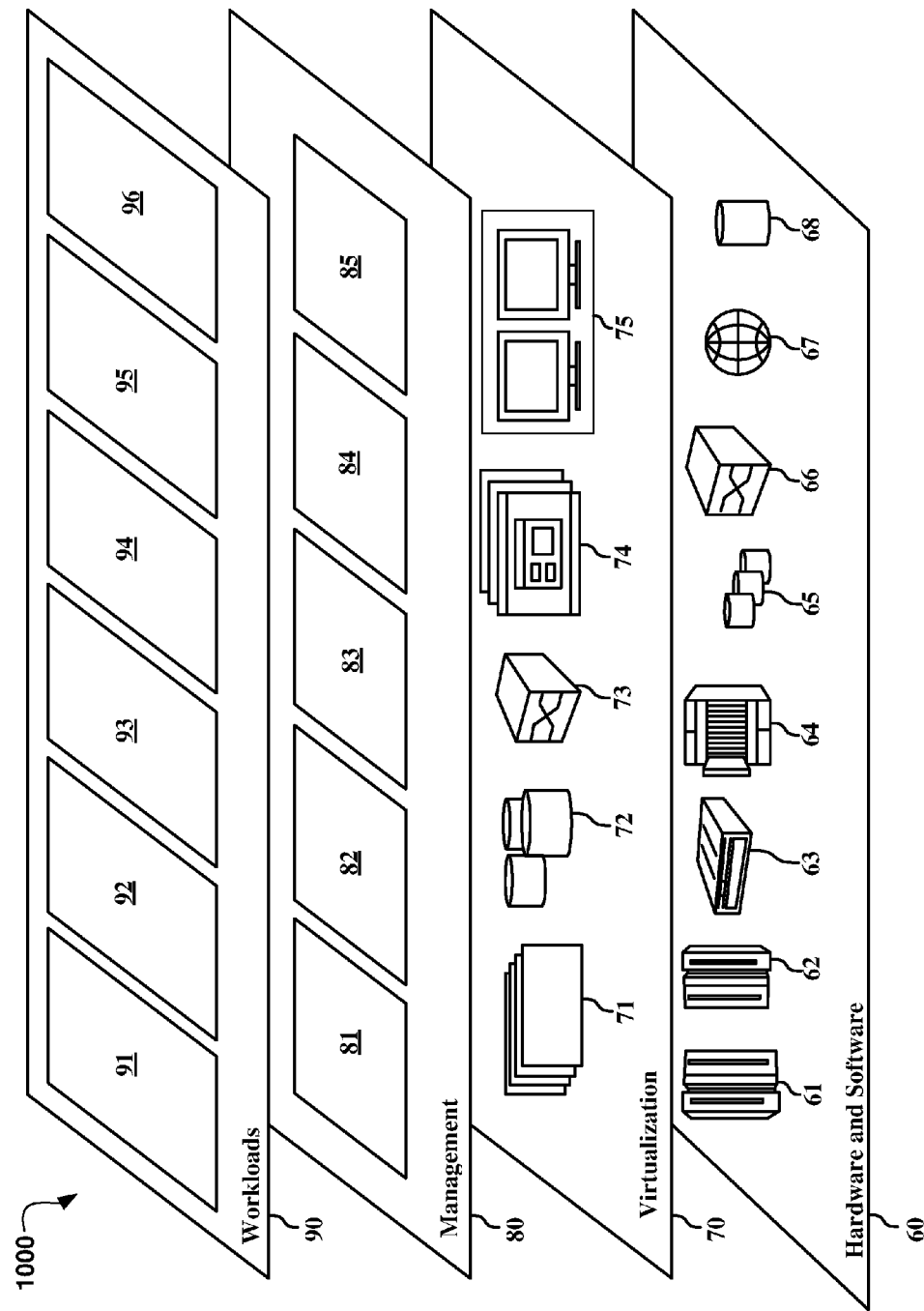
FIG. 10 is a block diagram of functional layers of the illustrative cloud computing environment of FIG. 9, in accordance with an embodiment of the present disclosure.

Referring now to FIG. 10 a set of functional abstraction layers 1000 provided by cloud computing environment 950 (FIG. 9) is shown. It should be understood in advance that the components, layers, and functions shown in FIG. 10 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and automated robotic filtration program 96. Automated robotic filtration program 96 may include dispatching robotic filters 208 (FIG. 2) to a contaminated zone (e.g., zone 206*a* (FIG. 2)) within a data center 200 (FIG. 2) when air data collected by sensors (e.g., sensor 202*a* (FIG. 2)) distributed throughout the data center 200 (FIG. 2) satisfies a threshold value. Furthermore, the appropriate scope to which the automated robotic filtration program 96 should be set to may be based on received air data.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A processor-implemented method for filtering a plurality of air, the method comprising:

receiving, by a processor, a plurality of air data collected by a sensor within a data center;

determining that a portion of the received plurality of air data corresponding to at least one zone within the data center satisfies a threshold;

transmitting a geographical location associated with the at least one zone that includes the sensor to a robotic filter based on determining that a portion of the received plurality of air data corresponding to the at least one zone within the data center satisfies a threshold; and dispatching the robotic filter to the transmitted geographic location to filter the at least one zone.

2. The method of claim 1, further comprising:

instructing the robotic filter to traverse the data center;

receiving, from the instructed robotic filter, a plurality of digital images of the data center collected by the instructed robotic filter;

locating the sensor based on the plurality received of digital images and detecting a frequency emitted by the located sensor;

organizing the data center into the at least one zone based on detecting the frequency emitted by the sensor; and generating a digital representation of the organized data center based on the at least one zone.

3. The method of claim 2, further comprising:

determining a path from the robotic filter to the at least one zone based on the transmitted geographic location and the generated digital representation of the data center; and instructing the robotic filter to traverse the determined path.

4. The method of claim 1, wherein the robotic filter has one or more filters and further comprises:

selecting a filter of the one or more filters based on the received plurality of air data; and instructing the robotic filter to use the selected filter to filter the at least one zone.

5. The method of claim 1, further comprising:

receiving a plurality of external air data collected from an external sensor located outside the data center;

comparing the received plurality of external air data to the received plurality of air data; and determining the geographical location within the at least one zone for the robotic filter to be oriented when filtering the at least one zone based on comparing the received plurality of external air data and the received plurality of air data.

6. The method of claim 1, further comprising:

transmitting, in response to the received plurality of air data satisfying the threshold, the received plurality of air data to a client device to be displayed within a user interface (UI).

7. The method of claim 6, further comprising:

determining an air filter utilized by the robotic filter has satisfied a filter threshold; and transmitting, in response to the determined air filter satisfying the filter threshold, a filter replacement indicator for display within the UI.

* * * * *